United States Patent
Pugh et al.

(10) Patent No.: US 7,474,985 B1
(45) Date of Patent: Jan. 6, 2009

(54) METHOD AND SYSTEM FOR DETECTING CHANGES IN DATA

(75) Inventors: Jamie K. Pugh, San Diego, CA (US); Patricia N. Miranda, San Diego, CA (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 595 days.

(21) Appl. No.: 10/423,568

(22) Filed: Apr. 25, 2003

(51) Int. Cl.
*G06F 3/01* (2006.01)

(52) U.S. Cl. .................... 702/179; 702/183; 702/188; 702/189

(58) Field of Classification Search ............... 702/66, 702/69, 75, 120, 143, 179, 182, 188, 189; 358/1.3, 1.9; 342/77; 700/31; 705/37; 600/505, 600/529

See application file for complete search history.

(56) References Cited

U.S. PATENT DOCUMENTS

| | | | | |
|---|---|---|---|---|
| 5,311,183 A * | 5/1994 | Mathews et al. | ........... | 342/26 B |
| 5,671,734 A * | 9/1997 | Pugh | ........................... | 600/301 |
| 5,687,733 A * | 11/1997 | McKown | ..................... | 600/505 |
| 5,850,622 A * | 12/1998 | Vassiliou et al. | ............... | 702/17 |
| 6,438,533 B1 | 8/2002 | Spackman et al. | ............. | 706/45 |
| 6,454,705 B1 | 9/2002 | Cosentino et al. | ........... | 600/300 |
| 2003/0160980 A1* | 8/2003 | Olsson et al. | ................. | 358/1.9 |

* cited by examiner

*Primary Examiner*—Eliseo Ramos Feliciano
*Assistant Examiner*—Felix E Suarez
(74) *Attorney, Agent, or Firm*—Ryan J. Friedl; Kyle Eppele

(57) ABSTRACT

A adaptive recursive method for detecting statistically significant changes in data performs steps that include: determining a mean and standard deviation for incoming data; flagging non-conforming data; detecting signals, trends, and/or shifts in the data, and resetting the mean and standard deviation under prescribed circumstances based on predetermined criteria, and then displaying statistics derived from the data.

12 Claims, 4 Drawing Sheets

METHOD AND SYSTEM FOR DETECTING CHANGES IN DATA

CROSS-REFERENCE TO RELATED APPLICATION

This application is related by common inventorship and subject matter to the commonly-assigned Patent Application No. 60/465,298, entitled "Method and Apparatus For Medical Data Surveillance," filed on even date herewith.

REFERENCE TO COMPUTER PROGRAM LISTING APPENDIX

Appendix 1 is a computer program listing, which is submitted on one compact disc that is referenced and incorporated herein by reference. Appendix 1 comprises the following eight files which were all created on 24 Mar. 2003: GetData.cpp (3 kB), GetData.h (1 kB), mean.cpp (30 kB), mean.h (3 kB), med.cpp (1 kB), med.h (1 kB), sock.cpp (2 kB), and sock.h (1 kB).

BACKGROUND OF THE INVENTION

A disease may be described in terms of a set of signs and symptoms. The sentinel event, a shift in a sign or symptom, is a shift toward or away from a state of "wellness". Medical signs comprise the set of measurable variables such as systolic blood pressure, diastolic blood pressure, temperature, weight, etc. Medical symptoms are a set of indicators such as headache, dizziness, blurred vision, etc. Although a shift in medical signs represents a change in health status, the resultant value may still be within a normal range. Information about the size, direction, time of the change, and time of the end of the change is important in determining health status, cause of disease and reaction to treatment.

A need therefore exists in the health care industry not only to monitor medical signs but to detect and report statistically significant changes in the medical signs that signal changes in the health status of medical patients.

SUMMARY OF THE INVENTION

A method for detecting statistically significant changes in changes in data, comprising the steps of: a) receiving and storing $i^{th}$ data in an array, where i is an index; b) determining a mean and standard deviation from consistent data for use with the $i^{th}$ data, and identifying and flagging non-conforming data from the array so that the consistent data exclude flagged non-conforming data if: i) no a priori mean and standard deviation are available, ii) if there are less than C consistent data stored in the array, iii) if a prior determined standard deviation equals zero, or iv) if a mean and standard deviation reset are required and there is at least C data in a subset of the array selected for use in the mean and standard deviation reset, where C is a positive integer; c) determining test statistics from the $i^{th}$ data using the mean and standard deviation determined in the step (b), wherein the test statistics include a signal length; d) flagging the $i^{th}$ data if the $i^{th}$ data is non-conforming; e) determining the direction of any signal, shift, or trend indicated by the data array at the $i^{th}$ data; f) determining if any signal, shift or trend is indicated by the $i^{th}$ data stored in the array at the $i^{th}$ data define a statistically significant signal, shift, or trend; g) displaying statistics representing the $i^{th}$ data stored in the array; and h) returning to the step (a) when $(i+1)^{th}$ data is available and if a continue process instruction is received. The method may be terminated if an end process instruction is received.

BRIEF DESCRIPTION OF THE DRAWINGS

Throughout the several views, like elements are referenced using like references.

DESCRIPTION OF THE PREFERRED EMBODIMENT

Figure 1:
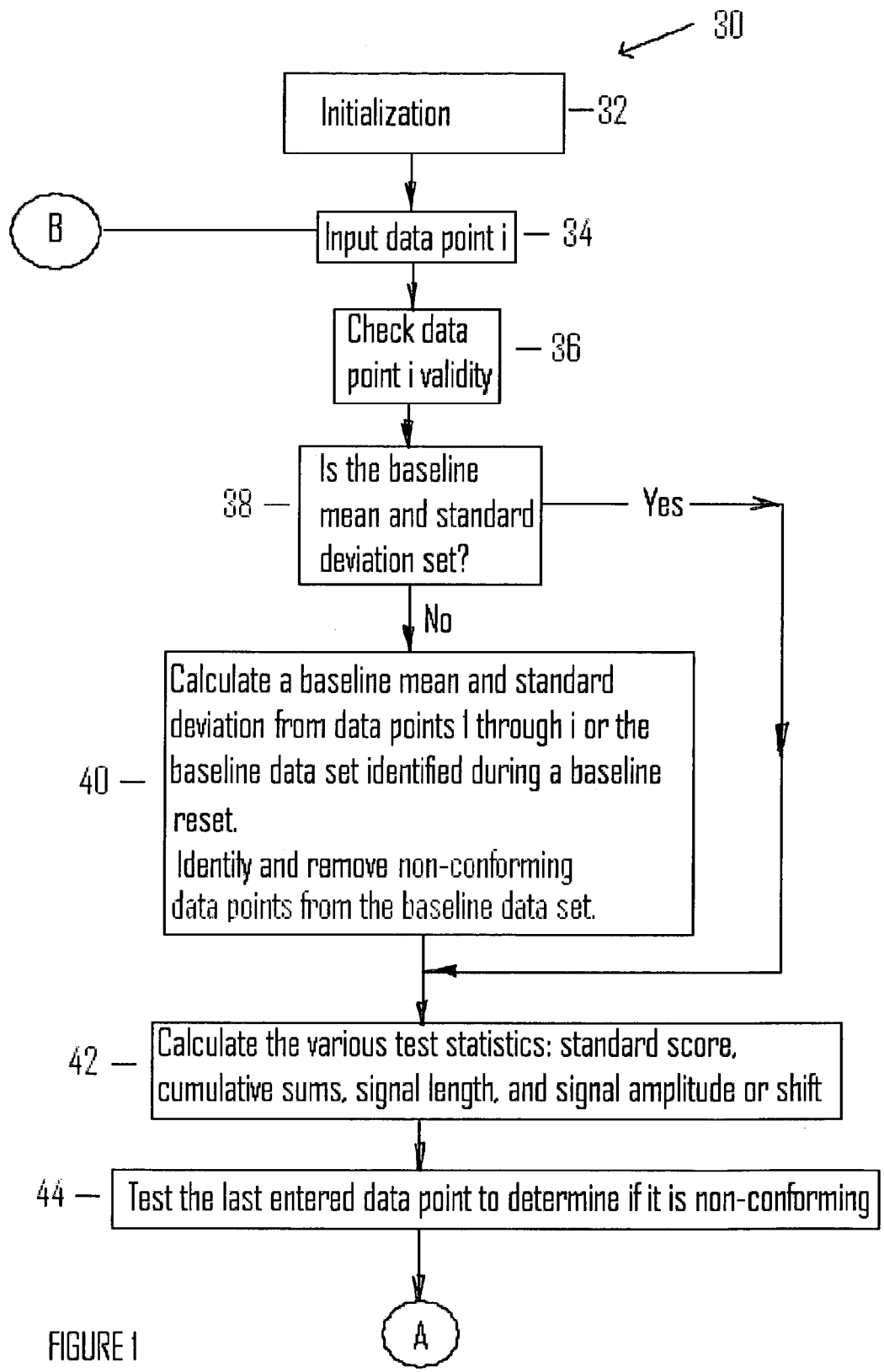
FIGS. 1 and 2 show a flow chart that represents a method for detecting changes in data which embodies various features of the present invention.
Figure 2:
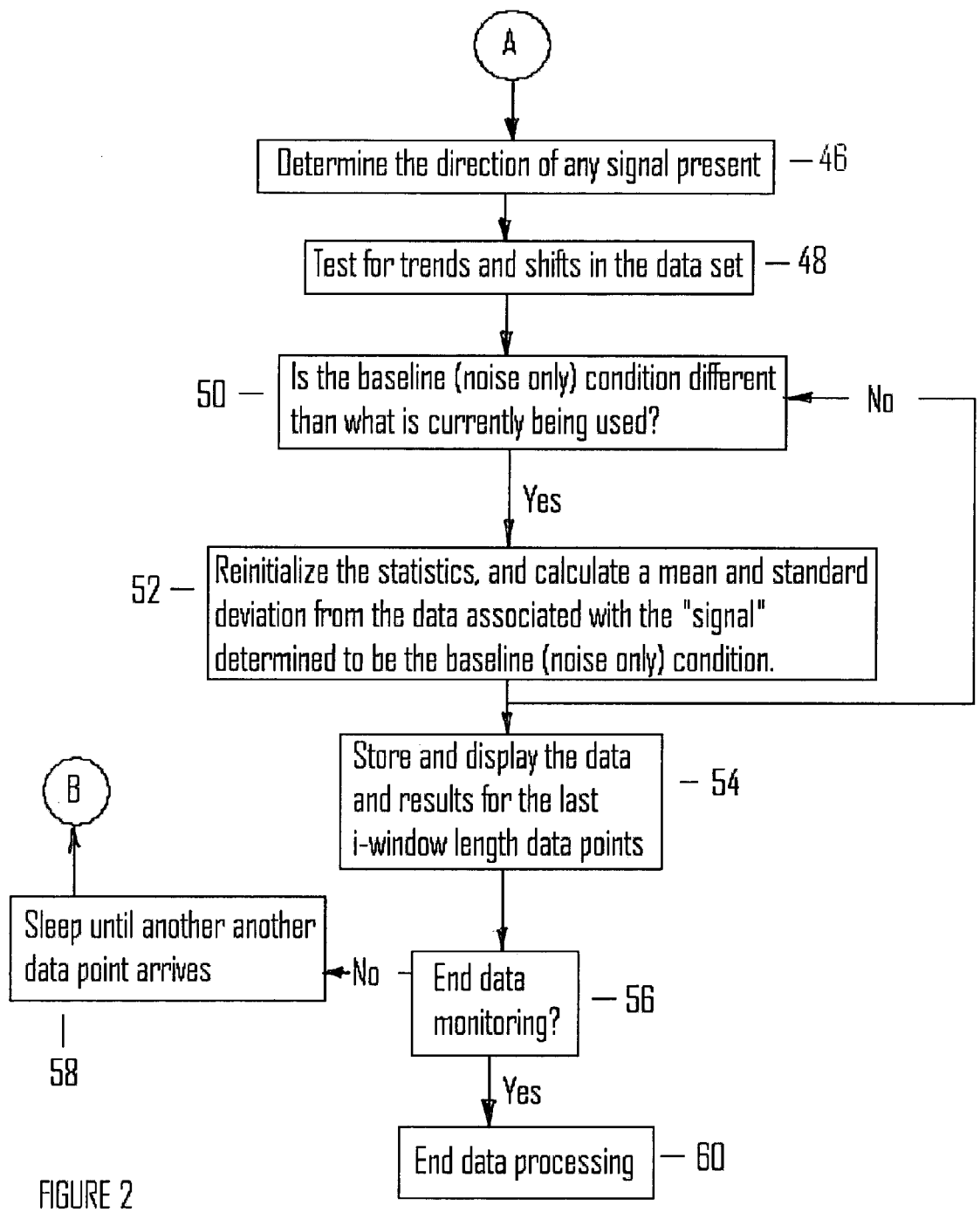

Referring to FIGS. 1 and 2, there is illustrated a method 30 for detecting statistically significant changes in data. Method 30 may be used for detecting changes in health related data of populations, as for example, the onset of a disease or a change in the health status of an individual. More generally, method 30 may be employed for detecting statistically significant changes in any type of time series data, such as acoustic data, infrared data, radar data, and other types of data, including imaging data in general.

Method 30 is initialized at step 34 where $i^{th}$ data is received and stored in an array. Next, at steps 38 and 40, method 30 determines a mean and standard deviation from consistent data that may be stored in the array for use with the $i^{th}$ data, and non-conforming data from the array are identified and flagged if: i) no a priori mean and standard deviation are available, ii) if there are less than a C number of consistent data stored in the array, iii) if a prior determined standard deviation equals zero, or iv) if a mean and standard deviation reset are required and there is at least C data in a subset of the array selected for use in the mean and standard deviation reset, where C is a positive integer, so that the consistent data exclude flagged non-conforming data.

Method 30 continues to step 42 where test statistics and a signal length are determined from the data, and the mean and standard deviation determined in at steps 38 and 40. Next at step 44, non-conforming data is flagged. Step 46 determines the direction of any signal, shift, or trend indicated by the data array at the $i^{th}$ data. Continuing to step 48, method 30 determines if any signal, shift, or trend is indicated by the data stored in the array at the $i^{th}$ data that indicate a statistically significant signal, shift, or trend. Statistics representing the data stored in the array are displayed at step 54 and in one embodiment, wherein such display may include color coded images that represent value ranges of the statistics. Method 30 returns to step 34 when $(i+1)^{th}$ data is available for input at step 34 and if a continue method instruction has been received. However, method 30 is terminated if an end method instruction is received.

Method 30 may further include the step of defining a data set from the statistically significant signal, shift, or trend, and signal length; and resetting the mean and standard deviation from the data stored in the array that correspond with the statistically significant signal, shift, or trend if i) the signal length includes at least a C number of data; ii) the signal, shift, or trend is statistically significant; and iii) if the signal, shift, or trend satisfies predetermined conditions. Such statistics may represent variables which include: the standard deviation, mean, signal length, signal amplitude, a standard score, cumulative sums, signal direction, an outlier, non-conforming data flags, and the flagged data.

A more detailed discussion of the mathematics associated with method 30 is described below with reference to FIGS. 1 and 2. Method 30 begins at step 32 where process values are initialized. Then, the first data, or data point, $x_1$, from a data set comprised of a time series of $x_1, \ldots, x_m$ data is input to method 30 at step 34, where 1 is the index of the first data point, and m is a positive integer that represents the number of data points that have been input into the method 30 method. In one embodiment, the data set may represent health characteristics, i.e., medical signs of an individual. At step 36, the validity of the data is checked, whereupon data is removed from further consideration that does not meet end-user criteria. At step 38, a check is made to determine if an acceptable baseline mean and standard deviation has been determined and is available for use. At step 40 if an acceptable baseline mean and standard deviation are not available, the baseline mean and standard deviation are derived from the first n incoming data points or the baseline data set identified during a baseline reset, where n is the current number of data points entered if the baseline mean and standard deviation are not set and is the last data point used to create an acceptable baseline mean and standard deviation after they are set the first time at step 40. The baseline mean and standard deviation are not available if they have not been provided during initialization of method 30, there is insufficient data, or prior values of the mean and standard deviation are to be reset, but are not yet determined. During this step, non-conforming data points are identified and removed in the baseline data set. At step 40, a variable r is set equal to the number of data points removed from consideration either a priori by the end-user or because they were found to be non-conforming data points. Step 40 further sets the mean and standard deviation and flags and removes non-conforming data points as detailed below. On the first data point (also referenced herein as data) entered, step 40 sets the mean equal to the data point value and the standard deviation to zero. On the second data point entered, step 40 sets the mean equal to the average of the first and second data point and the standard deviation to zero. Thereafter the mean and standard deviation are calculated as described below. Let $$f = \sqrt{\frac{n-r}{n-r+1}},$$

where n represents the current number of data points being considered, $n \leq m$, and r represents the number of data points that have been withdrawn from the data set. The value f used in the method 30 processing is an approximate ratio of the standard normal threshold and the t-test threshold, $\hat{t}_i$, associated with the degrees of freedom in the mean and standard deviation calculations, where $$\hat{t}_i = (f)\left(\frac{X_i - \text{mean}}{sd}\right).$$

In an alternative embodiment this approximation is replaced with the actual ratio.

$$R(X_i) = 0, \text{ if } \sqrt{\frac{n-r}{n-r+1}} \left|\frac{X_i - \text{mean}}{sd}\right| \geq \delta;$$

and $=X_i$, otherwise $$\text{mean} = \frac{\sum_{i=1}^{n} R(x_i)}{n-r} \text{ and } sd = \sqrt{\frac{\sum_{i=1}^{n} (R(x_i) - \text{mean})^2}{n-r-1}}.$$

Then the $x_1, \ldots, x_n$ data points of the baseline data set are tested for non-conforming data points using, by way of example, four Shewhart tests. The $i^{th}$ data point is flagged as a non-conforming data point when $$\sqrt{\frac{n-r}{n-r+1}} \left|\frac{X_i - \text{mean}}{sd}\right| \geq \delta,$$

where $\delta$ represents a constant having a value selected to suit the requirements of a particular application. The four Shewhart non-conforming data flagging tests are performed as described below:

A positive outlier is declared if $$\sqrt{\frac{n-r}{n-r+1}} \left(\frac{X_i - \text{mean}}{sd}\right) \geq \delta.$$

A positive burst is declared if $$\sqrt{\frac{n-r}{n-r+1}} \left(\frac{X_i - \text{mean}}{sd}\right) \geq \gamma,$$

where $\gamma$ represents a constant having a value selected to suit the requirements of a particular application. A negative outlier is declared if $$\sqrt{\frac{n-r}{n-r+1}} \left(\frac{X_i - \text{mean}}{sd}\right) \leq -\delta.$$

A negative burst is declared if $$\sqrt{\frac{n-r}{n-r+1}} \left(\frac{X_i - \text{mean}}{sd}\right) \leq -\gamma.$$

In one embodiment, by way of example, where $\gamma > \delta$, $\delta$ equals 2 and $\gamma$ equals 3. When a reset baseline condition has occurred, a new subset of the incoming data set, $x_{k+1} \ldots, x_L$, is used instead and r is set to the number of data points removed by the end-user plus the number of non-conforming data points in this new data set. If removal of a data point would cause the standard deviation to be zero, the data point is retained. Also, an adjustment in the non-conforming data point removal may be made when the data is discrete instead of continuous. Thus the mean and standard deviation may be, when needed, calculated and reset a number of times during the method 30 processing.

After obtaining the mean and standard deviation values at step 40, the method 30 continues to step 42 and applies the following statistical tests to the revised data set as detailed in greater detail herein: two fast initial response maximum cumulative sums (FIR MAX CUSUM), two maximum cumulative sums (MAX CUSUM), and four Shewhart statistical tests to the data set for detecting a change in state of the data. In one embodiment of the invention, the data may represent the number or rate of occurrence of individuals in a population with one or more symptoms such as fever, chills, itching, and vomiting. In this implementation, if a change in population health state is indicated, then the method 30 displays the new population health statistics on a display.

At step 42, the following test statistics are determined: an approximate standard score, FIR MAX CUSUM upper and lower values, MAX CUSUM upper and lower values, signal length, and signal amplitude. The approximate standard score is $$\hat{t}_i = (f)\left(\frac{X_i - \text{mean}}{sd}\right)$$

where f is the approximate ratio of the standard normal threshold and the t-test threshold associated with the degrees of freedom in the mean and standard deviation calculations. In one embodiment, $\beta$ is set equal to a constant, as for example 0.5, and H is set equal the threshold used in the CUSUM statistic tests, where H is a constant chosen such that the reciprocal of the average run length equals the desired probability of false alarm. The CUSUM upper sum is $SH_i=\max(SH_{i-1}+\hat{t}_i-\beta,0)$, and the MAX CUSUM upper sum is $$SH\max_j = \max_{i=1,\ldots j}(SH_i).$$

where $SH_0=0, \beta$ is a constant selected to suit the requirements of a particular application. The CUSUM lower sum is $SL_i=\max(SL_{i-1}-\hat{t}_i-\beta,0)$, and the MAX CUSUM lower sum is $$SL\max_j = \max_{i=1,\ldots j}(SL_i)$$

where $SL_0=0$. The FIR CUSUM upper sum is $FIRSH_i=\max(FIRSH_{i-1}+\hat{t}_i0=\beta,0)$, and the FIR MAX CUSUM upper sum is $$FIRSH\max_j = \max_{i=1,\ldots j}(FIRSH_i)$$

where $FIRSH_0=H/2$ and H is the threshold used in the CUSUM statistic tests. The FIR CUSUM lower sum is, and the FIR MAX CUSUM lower sum is $$FIRSL\max_j = \max_{i=1,\ldots j}(FIRSL_i),$$

where $FIRSL_0=H/2$ and H represents the threshold used in the CUSUM statistic tests.

At step 42, the method 30 estimates the signal length, shift or trend, the index of the signal starting point, and the data point index of the signal ending point as follows: The upper signal length (upward signal, shift, or trend) estimate equals zero if the CUSUM upper sum is less than or equal to zero otherwise add one to the upper signal (upward signal, shift, or trend) length estimate. In one embodiment, if the CUSUM upper sum decreases at least four times in a row, the CUSUM upper sum and the MAX CUSUM upper sum are reset. The starting point in the signal (upward signal, trend, or shift) is the index of the data point where the signal length is one, K, and the ending point in the signal (upward signal, trend, or shift) is the index of the data point where the MAX CUSUM upper sum reached its maximum value, L. The lower signal length (downward signal, shift or trend) equals zero if the CUSUM lower sum is less than or equal to zero otherwise add one to the lower signal (downward signal, shift, or trend) length. If the CUSUM lower sum decreases at least, by way of example, four times in a row, reset the CUSUM lower sum, and the MAX CUSUM lower sum. The starting point in the signal (downward signal, trend, or shift) is the index of the data point where the signal length (downward signal, trend, or shift) is one and the ending point in the signal (downward signal, trend, or shift) is the index of the data point where the MAX CUSUM lower sum reached its maximum value. In one embodiment, if the FIR CUSUM upper sum decreases at least four times in a row, reset the FIR CUSUM upper sum, and the FIR MAX CUSUM upper sum. However, if the FIR CUSUM lower sum decreases at least four times in a row, reset the FIR CUSUM lower sum, and the FIR MAX CUSUM lower sum. The signal length may include a non-conforming data point, shift, trend, or function that is above the mean.

The positive signal amplitude or upward trend, or shift for the $i^{th}$ data point is estimated as follows:

$$shift_{i,upper} = \left(\frac{SH_i}{length_{i,upper}} + \beta\right)(f)(sd).$$

The negative signal amplitude or downward trend or shift for the $i^{th}$ data point is estimated as follows:

$$shift_{i,lower} = \left(\frac{SL_i}{length_{i,lower}} + \beta\right)(f)(sd).$$

Continuing to step 44, four Shewhart tests are conducted on the current $i^{th}$ data point, where i is an index, to determine if it is a non-conforming data point and flags its condition. The four Shewhart non-conforming data flagging tests are described below. In the first Shewhart test, a positive outlier is declared if:

$$\sqrt{\frac{n-r}{n-r+1}}\left(\frac{X_i - \text{mean}}{sd}\right) \geq \delta.$$

In the second Shewhart test, a positive burst is declared if $$\sqrt{\frac{n-r}{n-r+1}}\left(\frac{X_i - \text{mean}}{sd}\right) \geq \gamma.$$

In the third Shewhart test, a negative outlier is declared if $$\sqrt{\frac{n-r}{n-r+1}}\left(\frac{X_i - \text{mean}}{sd}\right) \leq -\delta.$$

In the fourth Shewhart test, a negative burst is declared if $$\sqrt{\frac{n-r}{n-r+1}}\left(\frac{X_i - \text{mean}}{sd}\right) \leq -\gamma.$$

In one embodiment for example, where $\gamma > \delta$, $\delta = 2$ and $\gamma = 3$.

In step 46, method 30 determines the direction of any signal, shift, or trend indicated by the data at the time of the current data point. If the CUSUM upper sum, $SH_i = \max(SH_{i-1} + \hat{t}_i - \beta, 0)$, is greater than the CUSUM lower sum, $SL_i = \max(SL_{i-1} - \hat{t}_i - \beta, 0)$, the signal, shift, or trend is above the current baseline mean and is declared to be increasing. If the CUSUM upper sum, $SH_i = \max(SH_{i-1} + \hat{t}_i - \beta, 0)$, is less than the CUSUM lower sum, $SL_i = \max(SL_{i-1} - \hat{t}_i - \beta, 0)$, then the value of the signal, shift, or trend is below the current baseline mean and is declared to be decreasing. If the CUSUM upper and lower sums are equal, the signal shift or trend is declared to be neither increasing nor decreasing.

At step 48, method 30 determines if a statistically significant positive signal trend or shift, or negative signal trend or shift is occurring, and may reset the all of the CUSUM and FIR CUSUM summers. If $FIRSH_i \geq H$ a statistically significant positive signal, trend, or shift is declared, and if $FIRSL_i > H$ a statistically significant negative signal, trend, or shift is declared.

Step 50 determines if the baseline mean and standard deviation needs to be reset. The need to reset the baseline mean and standard deviation may occur if the initial data points used in calculating the mean and standard deviation contained a signal shift or trend having valid data and did not consist of only noise. The resetting of the baseline mean and standard deviation may also indicate an improvement in a patient's condition. For example a patient's drop in mean diastolic value from 105 to 100, although relatively high, is an improved mean. It may also be desirable to monitor for a continued decrease in diastolic values.

Method 30 at step 52 resets the baseline data set, mean, and standard deviation based on the "signal trend or shift," data points with indices K through L that have been determined to be the correct or current noise only baseline data set as follows:

$$\text{mean} = \frac{\sum_{i=K}^{L} x_i}{L-K+1} \text{ and } sd = \sqrt{\frac{\sum_{i=K}^{L}(x_i - \text{mean})^2}{L-K}}.$$

Method 30 at step 54 displays the results for the current data point. Continuing to step 56, method 30 determines if the monitoring is to continue or end. At step 58, the method 30 determines if another data point is available for processing or if the method needs to wait for the arrival of another data point. When another data point is available, the method returns to step 34. At step 60 method 30 ends the data processing and stops.

In an embodiment, method 30 may contain an additional step that reconstructs or extracts the signal, trend, or shift indicated by data points K through L on the ith data point using methods known to the art such as polynomial regression line fit.

Figure 3:
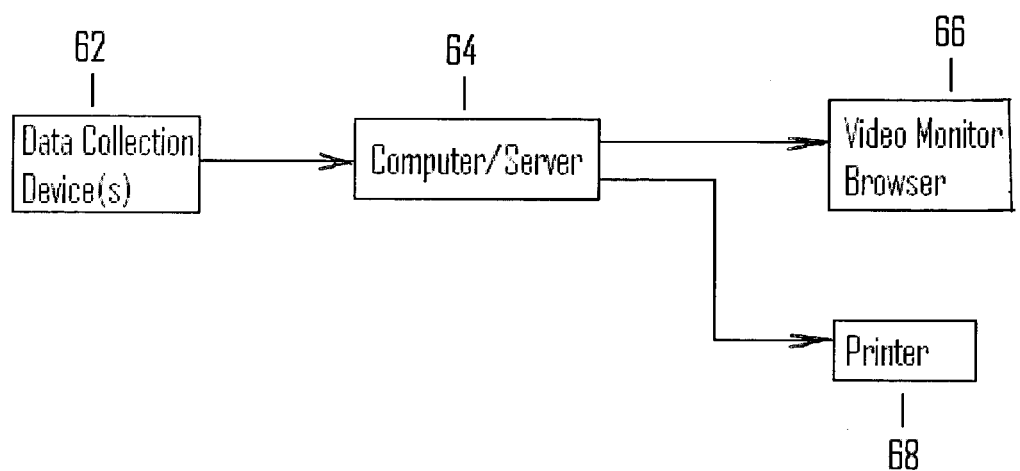
FIG. 3 shows a computer for implementing the method shown in FIGS. 1 and 2 that is connected to input and display devices.
Figure 4:
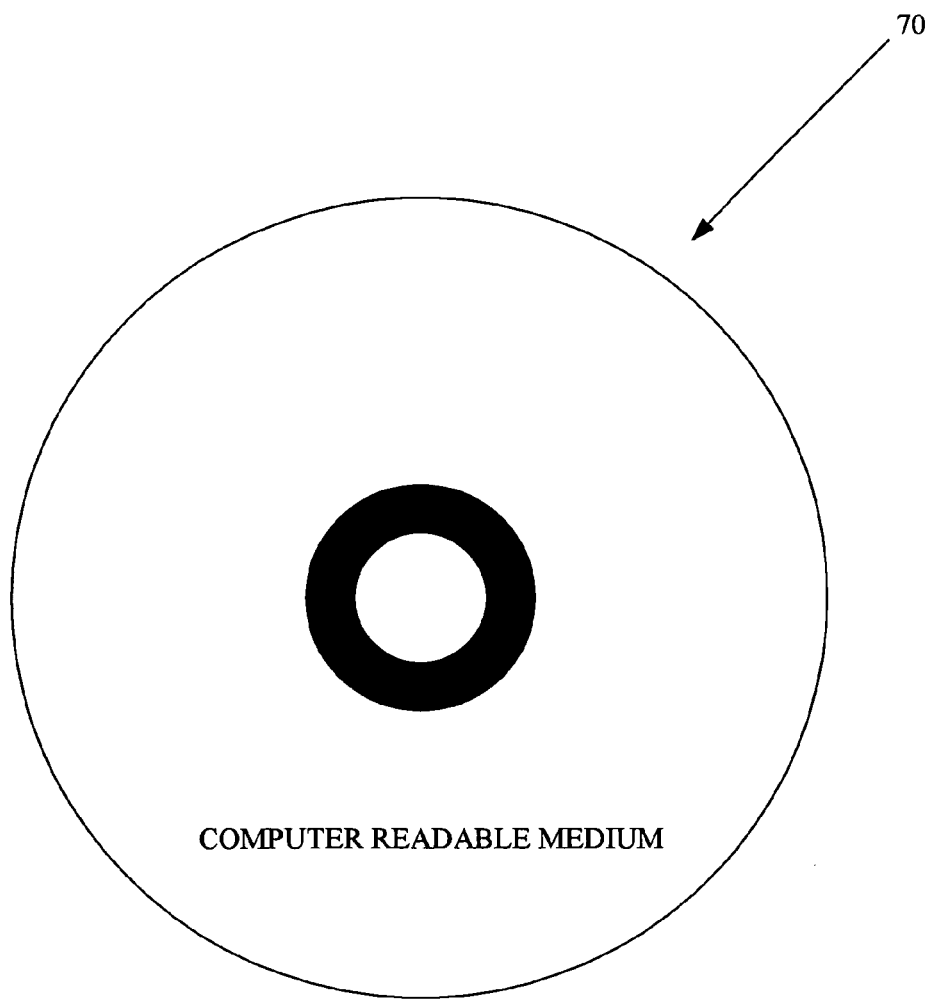
FIG. 4 shows a computer readable media on which a series of machine-readable instructions are encoded that may be read by a digital computer for implementing the method illustrated in FIGS. 1 and 2.

Referring to FIGS. 3 and 4, method 30 may be implemented by a digital computer 64 as a sequence of computer-readable program code that is embodied on a computer readable medium 70 as shown in FIG. 4, such as a compact disc 70. One or more data collection devices 62 may provide data input at step 34 and a process wake up alert at step 58. The data collection devices may be selected from the group that includes a sensor, another computer, database server, data file, or buffer. Computer 64 may provide display output at step 54 to one or more display devices such as video monitor/web browser 66 and/or printer 68. However, it is to be understood that the computer readable medium may also be implemented as a zip disc, optical disc, magnetic media, and the like.

Examples of such computer implemented steps for implementing method 30 are provided in Appendix 1 which is a compact disc that contains the files: GetData.cpp, GetData.h, mean.cpp, mean.h, med.cpp, med.h, sock.cpp, and sock.h. These files were written, by way of example, in C++. However, it is to be understood that these computer implemented steps may also be written using other programming languages.

Obviously, many modifications and variations of the invention described herein are possible in light of the above teachings. For example, instead of performing a CUSUM algorithm, method 30 may employ other mathematical techniques such as a moving average, linear regression, an auto-recursive method, and other well known techniques for determining signals, trends, or shifts in data sets. It is therefore to be understood that within the scope of the appended claims, the method described herein may be practiced otherwise than as specifically described.

We claim:

1. A method for detecting statistically significant changes in data, comprising the steps of:
   a) receiving and storing $i^{th}$ data in an array, where i is an index;
   b) determining a mean and standard deviation from consistent data for use with said $i^{th}$ data, and identifying and flagging non-conforming data from said array so that said consistent data exclude flagged non-conforming data if: i) no a prior mean and standard deviation are available, ii) if there are less than C consistent data stored in said array, iii) if a prior determined standard deviation equals zero, or iv) if a mean and standard deviation reset are required and there is at least C data in a subset of said array selected for use in said mean and standard deviation reset, where C is a positive integer;

c) determining test statistics from said $i^{th}$ data and said mean and standard deviation determined in said step (b), wherein said test statistics include a signal length;

d) flagging said $i^{th}$ data if said $i^{th}$ data is non-conforming;

e) determining a direction of any signal, shift, or trend indicated by said data array at said $i^{th}$ data;

f) determining if any said signal, shift, or trend is indicated by said $i^{th}$ data stored in said array at said $i^{th}$ data define a statistically significant signal, shift, or trend;

g) displaying statistics representing said $i^{th}$ data stored in said array; and h) returning to said step (a) when $(i+1)^{th}$ data is available and if a continue process instruction is received.

2. The method of claim 1 further including the step of terminating said method if an end process instruction is received.

3. The method of claim 1 wherein said step (g) includes displaying color coded images that represent value ranges of said statistics.

4. The method of claim 1 further including the step of defining a data set from said statistically significant signal, trend, or shift and said signal length, and resetting said mean and standard deviation from said $i^{th}$ data stored in said array that correspond with said statistically significant signal, trend, or shift if i) said signal length includes at least C data; ii) said signal, shift, or trend is statistically significant; or iii) if said signal, shift, or trend satisfy predetermined conditions.

5. The method of claim 2 wherein said statistics represent variables from the group that includes said standard deviation, said mean, a length of said signal, amplitude of said signal, said shift trend, a standard score, cumulative sums, signal direction, an outlier, non-conforming data flags, said flagged $i^{th}$ data.

6. The method of claim 1 wherein said $i^{th}$ data represents medical signs.

7. The method of claim 1 wherein said $i^{th}$ data represents data selected from the group that includes acoustic data, infrared data, radar data, and imaging data.

8. A computer program product, comprising:

a computer usable medium having computer readable program code means embodied therein for detecting statistically significant changes in data, said computer readable program code means including:

a) first computer readable program means for causing said computer to receive and store $i^{th}$ data in an array, where i is an index;

b) second computer readable program means for causing said computer to determine a mean and standard deviation from consistent data for use with said $i^{th}$ data, and to identify and flag non-conforming data from said array so that said consistent data exclude flagged non-conforming data if: i) no a prior mean and standard deviation are available, ii) if there are less than C consistent data stored in said array, iii) if a prior determined standard deviation equals zero, or iv) if a mean and standard deviation reset are required and there is at least C data in a subset of said array selected for use in said mean and standard deviation reset, where C is a positive integer;

c) third computer readable program means for causing said computer to determine test statistics from said $i^{th}$ data and said mean and standard deviation determined by said second computer readable program means, wherein said test statistics include a signal length;

d) fourth computer readable program means for causing said computer to flag said $i^{th}$ data if said $i^{th}$ data is non-conforming;

e) fifth computer readable program means for causing said computer to determine the direction of any signal, shift, or trend indicated by said data array at said $i^{th}$ data;

f) sixth computer readable program means for causing said computer to determine if any signals, shifts or trends is indicated by said $i^{th}$ data stored in said array at said $i^{th}$ data define a statistically significant signal, shift, or trend;

g) seventh computer readable program means for causing said computer to display statistics representing said $i^{th}$ data stored in said array; and h) eighth computer readable program means for causing said computer to return to said first computer readable program means when $(i+1)^{th}$ data is available and if a continue process instruction is received.

9. The computer program product of claim 8 further including a ninth computer readable program means for causing said computer to terminate a computer program implemented by said computer readable program code means if an end process instruction is received.

10. A system for detecting statistically significant changes in data, comprising:

a computer for executing a sequence of computer readable instructions for performing the computer executable steps of:

a) receiving and storing $i^{th}$ data in an array, where i is an index;

b) determining a mean and standard deviation from consistent data for use with said $i^{th}$ data, and identifying and flagging non-conforming data from said array so that said consistent data exclude flagged non-conforming data i) if no a prior mean and standard deviation are available, ii) if there are less than C consistent data stored in said array, iii) if a prior determined standard deviation equals zero, or iv) if a mean and standard deviation reset are required and there are at least C data in a subset of said array selected for use in said mean and standard deviation reset, where C is a positive integer;

c) determining test statistics from said $i^{th}$ data and said mean and standard deviation determined in said step (b), wherein said test statistics include a signal length;

d) flagging said $i^{th}$ data if said $i^{th}$ data is non-conforming;

e) determining the direction of any signal, trend or shift indicated by said data array at said $i^{th}$ data;

f) determining if any signal, shift, or trend is indicated by said $i^{th}$ data stored in said array at said $i^{th}$ data define a statistically significant signal, trend or shift;

g) displaying statistics representing said $i^{th}$ data stored in said array; and h) returning to said step (a) when $(i+1)^{th}$ data is available, and if a continue process instruction is received.

11. The system of claim 10 further including the step of terminating said sequence of computer readable instructions if an end process instruction is received.

12. The system of claim 10 wherein said step (g) includes displaying color coded images that represent value ranges of said statistics.

* * * * *